(12) United States Patent
Hiraoka et al.

(10) Patent No.: US 10,154,895 B2
(45) Date of Patent: Dec. 18, 2018

(54) ACTUATOR

(71) Applicant: Panasonic Intellectual Property Management Co., Ltd., Osaka (JP)

(72) Inventors: Maki Hiraoka, Nara (JP); Katsuhiko Asai, Nara (JP); Yuriko Kaneko, Nara (JP); Hidekazu Arase, Hyogo (JP); Atsushi Omote, Osaka (JP)

(73) Assignee: PANASAONIC INTELLECTUAL PROPERTY MANAGEMEENT CO., LTD., Osaka (JP)

( * ) Notice: Subject to any disclaimer, the term of this patent is extended or adjusted under 35 U.S.C. 154(b) by 184 days.

(21) Appl. No.: 15/245,145

(22) Filed: Aug. 23, 2016

(65) Prior Publication Data
US 2017/0035550 A1 Feb. 9, 2017

Related U.S. Application Data

(63) Continuation of application No. PCT/JP2016/000974, filed on Feb. 24, 2016.

(30) Foreign Application Priority Data

Aug. 4, 2015 (JP) ................................. 2015-153998
Nov. 24, 2015 (JP) ................................. 2015-228329

(51) Int. Cl.
| F03G 7/06 | (2006.01) |
| A61F 2/08 | (2006.01) |
| A61F 7/00 | (2006.01) |
| A61L 27/16 | (2006.01) |
| A61L 27/30 | (2006.01) |
| A61L 27/50 | (2006.01) |

(52) U.S. Cl.
CPC .................. *A61F 2/08* (2013.01); *A61F 7/00* (2013.01); *A61L 27/16* (2013.01); *A61L 27/306* (2013.01);
(Continued)

(58) Field of Classification Search
CPC ... F03G 7/065; F03G 7/00; F03G 7/06; F03G 2730/00; F03G 2730/01; F03G 2730/02
(Continued)

(56) References Cited

U.S. PATENT DOCUMENTS

| 2008/0034750 A1* | 2/2008 | Gao ......................... F03G 7/065 60/527 |
| 2009/0009656 A1* | 1/2009 | Honda ..................... F03G 7/065 348/372 |

(Continued)

FOREIGN PATENT DOCUMENTS

WO 2014/022667 2/2014

OTHER PUBLICATIONS

International Search Report of PCT application No. PCT/JP2016/000974 dated May 24, 2016.
(Continued)

*Primary Examiner* — Mark Laurenzi
*Assistant Examiner* — Mickey France
(74) *Attorney, Agent, or Firm* — McDermott Will & Emery LLP

(57) ABSTRACT

The present invention provides an actuator, comprising a fiber and a temperature regulator capable of at least one of heating and cooling the fiber. The fiber is twisted around a longitudinal axis thereof. The fiber is folded so as to have a shape of a cylindrical coil. The fiber is formed of linear low-density polyethylene. The following mathematical formula (I) is satisfied: D/d<1 (I), where D represents a mean diameter of the cylindrical coil; and d represents a diameter of the fiber.

14 Claims, 9 Drawing Sheets

(52) U.S. Cl.
CPC ............... *A61L 27/50* (2013.01); *F03G 7/06* (2013.01); *A61F 2002/0894* (2013.01); *A61F 2210/0071* (2013.01); *A61F 2230/0069* (2013.01); *A61F 2230/0091* (2013.01); *A61F 2240/001* (2013.01); *A61L 2430/30* (2013.01)

(58) Field of Classification Search
USPC .................................... 60/527–529; 310/306
See application file for complete search history.

(56) References Cited

U.S. PATENT DOCUMENTS

| | | |
|---|---|---|
| 2012/0137672 A1 | 6/2012 | Pinto et al. |
| 2015/0152852 A1* | 6/2015 | Li .................. H02N 11/006 60/528 |

OTHER PUBLICATIONS

Maki Hiraoka et al., "Large strains and their polymer chain morphologies on coiled polymer fiber actuators" Symposium of the 24th Polymer material forum, disclosed on Nov. 26, 2015 (Whole sentence Translation).

The Extended European Search Report dated Jun. 21, 2018 for the related European Patent Application No. 16767126.2.

Madden John D W et al: "Twisted Lines : Artificial muscle and advanced instruments can be formed from nylon threads and fabric", IEEE Pulse, IEEE, USA, vol. 6, No. 1, Jan. 1, 2015 (Jan. 1, 2015), pp. 32-35, XP011570822.

\* cited by examiner

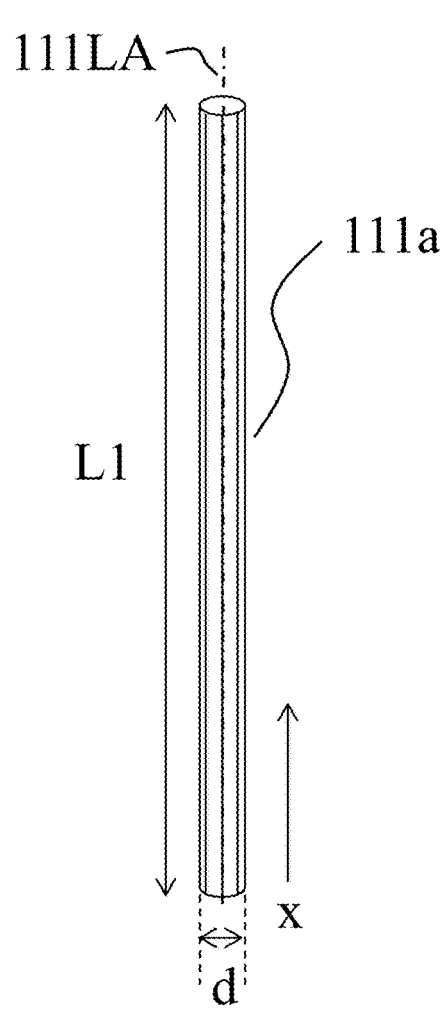
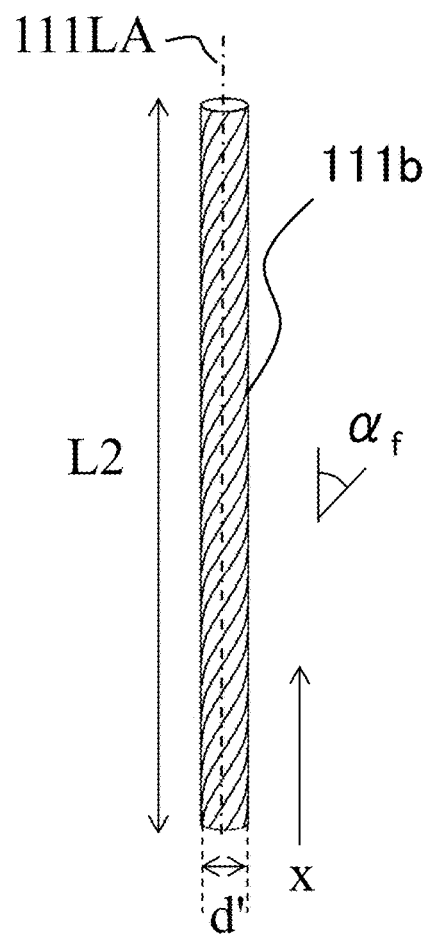
FIG. 2A
FIG. 2B

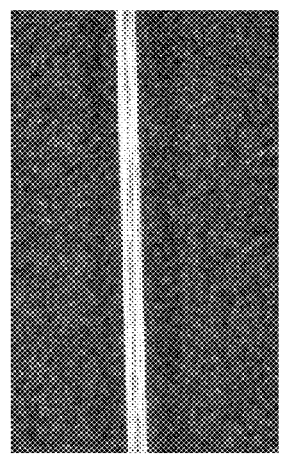 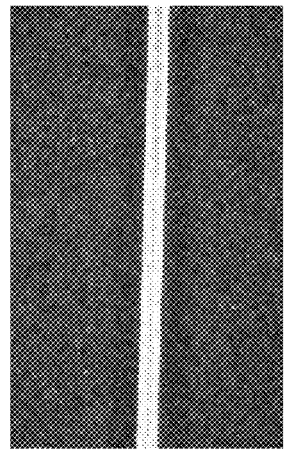
FIG. 5A　　　　　FIG. 5B
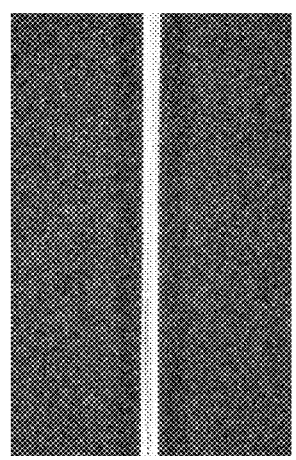 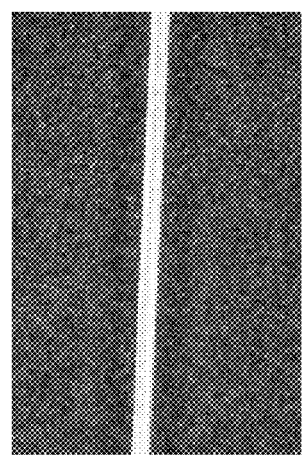
FIG. 5C　　　　　FIG. 5D

ACTUATOR

BACKGROUND

1. Technical Field

The present invention relates to an actuator.

2. Description of the Rerated Art

United States Pre-Grant Patent Application Publication No. 2015/0219078 discloses an actuator formed of a polymer fiber. In United States Pre-Grant Patent Application Publication No. 2015/0219078, the polymer fiber is twisted and folded. United States Pre-Grant Patent Application Publication No. 2015/0219078 is incorporated herewith by reference.

SUMMARY

An object of the present invention is to provide an actuator having a high displacement rate.

The present invention provides an actuator, comprising:
a fiber; and
a temperature regulator capable of at least one of heating and cooling the fiber, wherein
the fiber is twisted around a longitudinal axis thereof;
the fiber is folded so as to have a shape of a cylindrical coil;
the fiber is formed of linear low-density polyethylene; and
the following mathematical formula (I) is satisfied:

$$D/d<1 \quad (I)$$

where
D represents a mean diameter of the cylindrical coil; and
d represents a diameter of the fiber.

The spirits of the present invention includes a method for extending and contracting a fiber; the method comprising:
(a) heating the fiber to contract the fiber; wherein
the fiber is twisted around a longitudinal axis thereof;
the fiber is folded so as to have a shape of a cylindrical coil;
the fiber is formed of linear low-density polyethylene;
the following mathematical formula (I) is satisfied:

$$D/d<1 \quad (I)$$

where
D represents a mean diameter of the cylindrical coil; and
d represents a diameter of the fiber; and
the fiber is contracted along an axis direction of the cylindrical coil; and
(b) cooling the fiber to extend the fiber; wherein
the fiber is extended along the axis direction of the cylindrical coil.

The present invention provides an actuator having a high displacement rate.

BRIEF DESCRIPTION OF THE DRAWINGS

FIG. 2A shows a schematic view of a fiber 111a which is neither twisted nor folded.

FIG. 2B shows a schematic view of a fiber 111b which is twisted, however, is not folded.

FIG. 5A is a photograph showing the extended fiber 111a obtained in the inventive example 1.

FIG. 5B is a photograph showing the extended fiber 111a obtained in the comparative example 1A.

FIG. 5C is a photograph showing the extended fiber 111a obtained in the comparative example 2A.

FIG. 5D is a photograph showing the extended fiber 111a obtained in the comparative example 3A.

DETAILED DESCRIPTION OF THE EMBODIMENT

The embodiment of the present invention will be described with reference to the drawings.

(Terms)

First, the reference numbers added to the term "fiber" in the instant specification will be defined as below.

The term "fiber 111a" means a fiber which is neither twisted nor folded. See FIG. 2A. The fiber 111a may be referred to as "extended fiber 111a".

The term "fiber 111b" means a fiber which is twisted, however, is not folded. See FIG. 2B. The fiber 111b may be referred to as "twisted fiber 111b".

The term "fiber 111c" means a fiber which is twisted and folded. See FIG. 2C. The fiber 111c may be referred to as "folded fiber 111c".

The term "fiber 111" comprehensively includes the fibers 111a-111c.

In the instant specification, there is not a fiber which is folded, however, is not twisted.

(Embodiment)

Figure 1A:
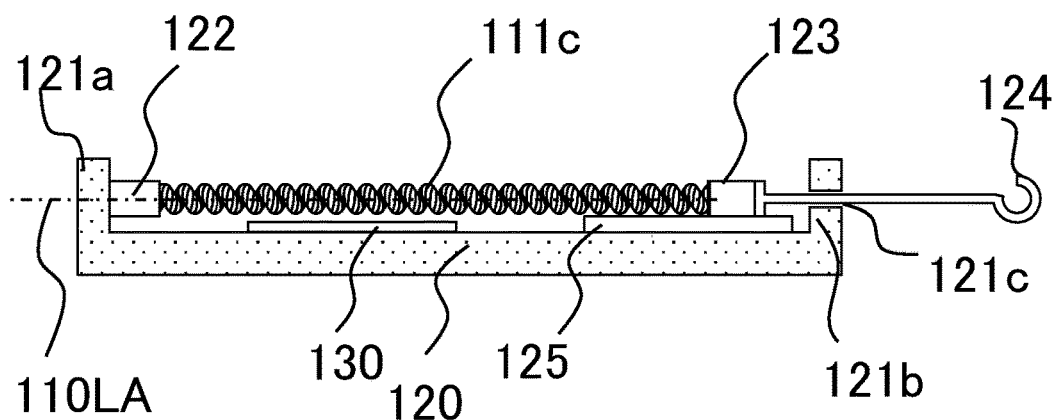
FIG. 1A shows a cross-sectional view of an actuator according to the present embodiment.

As shown in FIG. 1A, an actuator according to the present embodiment comprises a fiber 111c consisting of linear low-density polyethylene and a temperature regulator 130. The temperature regulator 130 is capable of at least one of heating and cooling the fiber 111c.

(Fiber)

The fiber 111c is twisted around the longitudinal axis thereof. The fiber 111c is folded so as to have a helix shape. In other words, the fiber 111c is folded so as to have a shape of a cylindrical coil.

First, a method for fabricating the fiber 111c used in the present embodiment will be described with reference to FIG. 2A FIG. 2C.

As shown in FIG. 2A, a fiber 111a having a length of L1 and a diameter of d is prepared. Needless to say, the fiber 111a is elongate and has a fiber axis 111LA. In FIG. 2A, the fiber 111a is neither twisted nor folded yet. The fiber axis 111LA is also a central axis of the fiber 111a and parallel to the x-axis direction.

Next, as shown in FIG. 2B, the fiber 111a is twisted. In this way, the fiber 111b is obtained. More specifically, one end of the fiber 111a is twisted around the fiber axis 111LA, while the other end of the fiber 111a is fixed so as not to be twisted around the fiber axis 111LA. In this way, the twisted fiber 111b is obtained. In FIG. 2B, the fiber 111b is twisted, however, is not yet folded. The fiber 111b has a length of L2. The fiber 111b has a diameter d' which is slightly greater than the diameter d. The fiber axis 111LA is parallel to the x-axis direction. The value of L2 is equal to or less than the value of L1.

The above-mentioned twists are continued in such a way that the one end of the fiber 111b is rotated many times around the fiber axis 111LA. As a result, as shown in FIG. 2C, the fiber 111 is folded while being rotated. More specifically, the fiber 111 is folded so as to have a length of L3 which is smaller than L1 and to have a mean diameter of D which is less than d. Also in this stage, the other end of the fiber 111 is fixed so as not to be twisted around the fiber axis 111LA. In this way, the fiber 111c which is twisted and folded is obtained. An angle $\alpha_f$ shown in FIG. 2B represents a fiber bias angle. The fiber bias angle $\alpha_f$ is a twist angle of the fiber 111 with regard to the fiber axis 111LA. The mean diameter D is obtained by subtracting the diameter d of the fiber from the external diameter D' of the cylindrical coil.

Figure 2C:
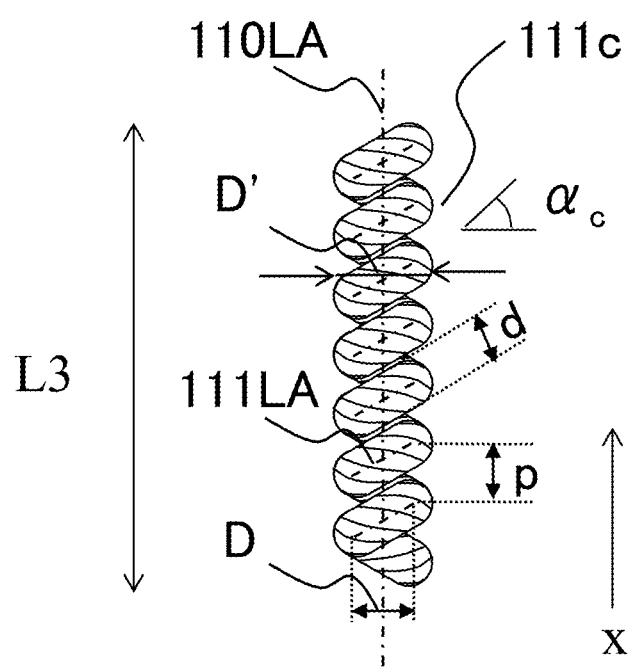
FIG. 2C shows a schematic view of a fiber 111c which is twisted and folded.

As shown in FIG. 2C, after the fiber 111 is folded, the fiber axis 111LA is no longer parallel to the x axis. The folded fiber 111c has a helix shape. In other words, the folded fiber 111c has a shape of a cylindrical coil. In other words, the folded fiber 111c has a shape of a spring. As shown in FIG. 2C, the coil has a pitch of p. The pitch p is equal to one period of the coil. See FIG. 2D.

Figure 2D:
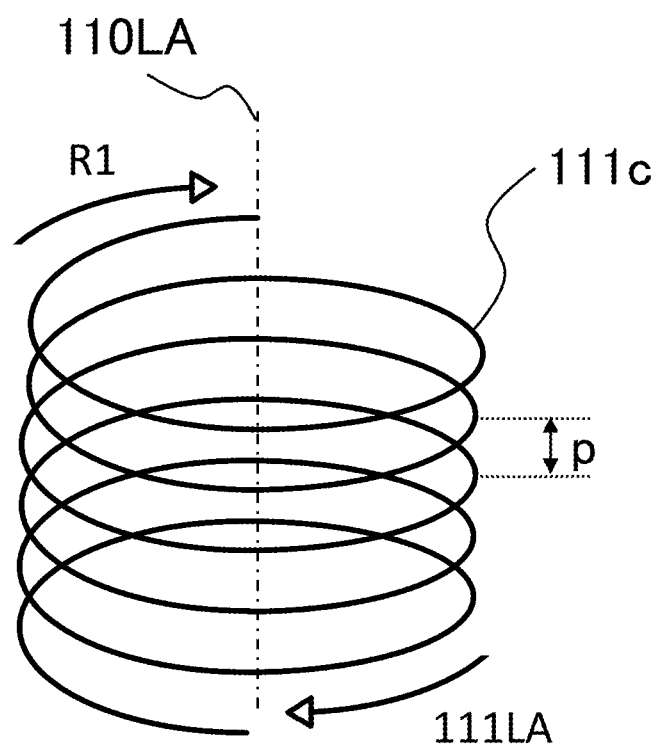
FIG. 2D shows a schematic view of a cylindrical coil formed of the folded fiber 111c.

As shown in FIG. 2D, the rotation direction R1 of the helix (i.e., the rotation direction R1 of the cylindrical coil) accords with the fiber axis iii LA of the folded fiber 111c . Needless to say, when the fiber 111 is twisted clockwise around the fiber axis 111LA in FIG. 2B, the fiber 111 is folded with rotating clockwise in FIG. 2C. Similarly, when the fiber 111 is twisted counterclockwise around the fiber axis 111LA in FIG. 2B, the fiber 111 is folded with rotating counterclockwise in FIG. 2C.

The cylindrical coil formed of the folded fiber 111c has a mean diameter of D. The cylindrical coil has a longitudinal axis 110LA. Hereinafter, the longitudinal axis 110LA of the cylindrical coil is referred to as a coil axis 110LA.

An angle $\alpha_c$ shown in FIG. 2C represents a coil bias angle. The coil bias angle $\alpha_c$ is formed between a plane perpendicular to the coil axis 110LA and the fiber axis 111LA of the folded fiber 111c.

In the present embodiment, the fiber 111 is formed of linear low-density polyethylene (hereinafter, referred to as "L-LDPE"). Since the fiber 111 is formed of linear low-density polyethylene, the folded fiber 111c has a spring index C of less than 1.

As well known, the spring index C is represented by the following mathematical formula (I):

$$C=D/d$$

where

D represents a mean diameter of the cylindrical coil formed of the folded fiber 111c, and d represents a diameter of the fiber 111.

It gets harder to extend the cylindrical coil with a decrease in the spring index C. In other words, the amount of the extension of the cylindrical coil is smaller with a decrease in the spring index C, in a case where a force F applied to the cylindrical coil along the axis direction (i.e., the longitudinal direction) of the cylindrical coil is constant.

On the other hand, the cylindrical coil is extended easily with an increase in the spring index C. In other words, the amount of the extension of the cylindrical coil is greater with an increase in the spring index C, in a case where a force F applied to the cylindrical coil along the axis direction (i.e., the longitudinal direction) of the cylindrical coil is constant.

Therefore, a cylindrical coil having a high spring index C is "soft" and a cylindrical coil having a low spring index C is "stiff". When the number of the twist of the fiber 111 around the fiber axis 111LA is increased, namely, when the number of the rotation of the fiber 111 around the fiber axis 111LA is increased, the spring index C of the obtained cylindrical coil is decreased. However, when the number of the twist (i.e., the number of the rotation) is increased too much, the fiber 111 is broken.

It is difficult to form a cylindrical coil having a spring index C of less than 1 by twisting a fiber formed of a resin other than linear low-density polyethylene (e.g., low-density polyethylene, high-density polyethylene, or nylon 66). This is because the fiber formed of a resin other than linear low-density polyethylene (e.g., low-density polyethylene) is broken due to its low durability against the load generated inside by the twist before the spring index C reaches less than 1. Alternatively, this is because the fiber formed of a resin other than linear low-density polyethylene (e.g., high-density polyethylene or nylon 66) has a spring index C of 1 or more. For more detail, see the examples and the comparative examples which will be described later.

The present inventors found through experiments that a fiber formed of linear low-density polyethylene is not broken even if its spring index C is less than 1.

A typical coil formed of metal may have a spring index C of not less than 4 and not more than 22 in light of its performance and manufacturing easiness. However, in the present embodiment, the cylindrical coil is formed of linear low-density polyethylene and has a small spring index C of less than 1. The small spring index C of less than 1 is required to achieve a high displacement rate which will be described later.

Linear low-density polyethylene may have a density of not less than 0.915 g/cm$^3$ and not more than 0.925 g/cm$^3$ and a weight-average molecular weight of not less than 50 kg/mol and not more than 200 kg/mol. Linear low-density polyethylene is composed of ethylene monomer units each represented by the chemical structural formula —$(CH_2—CH_2)_n$— (where n is a natural number) and α-olefin monomer units each represented by the chemical structural formula —$(CH_2—CHR)_m$— (where m is a natural number, and R represents a hydrocarbon group).

The molar ratio of the α-olefin monomer units to the ethylene monomer units may be not less than 2.5% and not more than 3.5%. In other words, the value of m/n may be not less than 0.025 and not more than 0.035. Each of the α-olefin monomer units may have a carbon number of not less than 4 and not more than 8. An example of R is —$CH_2CH_3$, —$CH_2CH_2CH_2CH_3$, —$CH_2CH(CH_3)CH_3$, or —$CH_2CH_2CH_2CH_2CH_2CH_3$.

(Base 120)

As shown in FIG. 1A, the actuator according to the present embodiment may comprise a plate-like base 120. The plate-like base 120 comprises a first protrusion 121a at one end thereof. The one end of the folded fiber 111c is fixed to the first protrusion 121a through a holding fixture 122. The plate-like base 120 comprises a second protrusion 121b at the other end. The other end of the folded fiber 111c is connected to one end of a rod 123. The second protrusion 121b has a through hole 121c. The rod 123 penetrates the through hole 121c. The rod 123 has a hook 124 at the other end thereof.

Figure 1B:
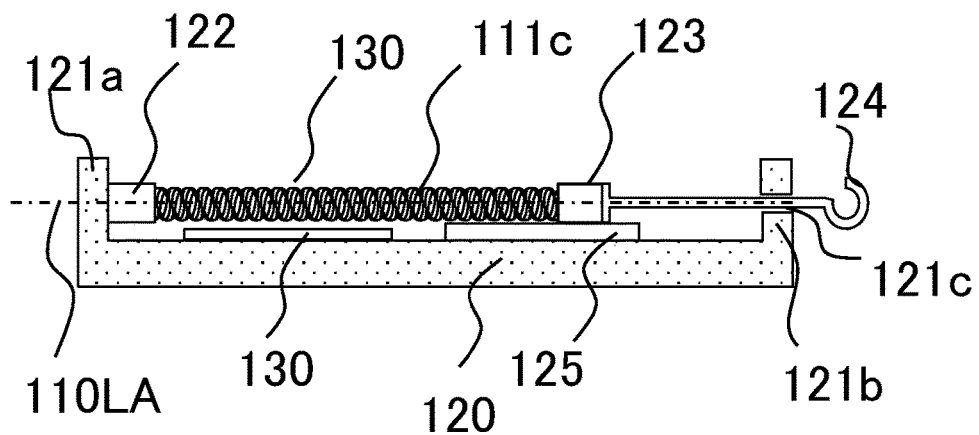
FIG. 1B shows a cross-sectional view of the actuator in the state where a fiber is contracted.

A plate-like slider 125 is located slidably on the plate-like base 120 between the plate-like base 120 and the one end of the rod 123. The plate-like slider 125 moves along the coil axis 110LA together with the extension and the contraction of the cylindrical coil formed of the folded fiber 111c. More specifically, when the folded fiber 111c is heated, as shown in FIG. 1B, the plate-like slider 125 also moves along the coil axis 110LA. In place of or together with the plate-like slider 125, a pulley or a guide tube may be used.

In FIG. 1A, the actuator comprises one fiber 111c. The actuator may comprise two or more fibers 111c. One fiber 111b may be obtained by integrally twisting two or more fibers 111a which are arranged parallel. One fiber 111c may be obtained by integrally twisting two or more twisted fibers 111b which are arranged parallel.

In order to prevent the twist and the fold of the fiber 111c from loosening, it is desirable that one end of the fiber 111c is fixed. In other words, it is desirable that the one end of the fiber 111c is fixed by the folding fixture 122.

(Temperature Regulator 130)

An example of the temperature regulator 130 is a heater or a cooler. The temperature regulator 130 may have at least one of the heater and the cooler. The temperature regulator 130 may have both of the heater and the cooler. An example of the cooler is a Peltier element. Hot water or cold water may be supplied to heat or cool the fiber 111c.

As shown in FIG. 1A, the temperature regulator 130 may be located between the fiber 111c and the plate-like base 120. In this case, the temperature regulator 130 has a shape of a thin plate. In other words, at least one of a heater and a Peltier element having a shape of a thin plate may be located between the fiber 111c and the plate-like base 120.

Figure 2E:
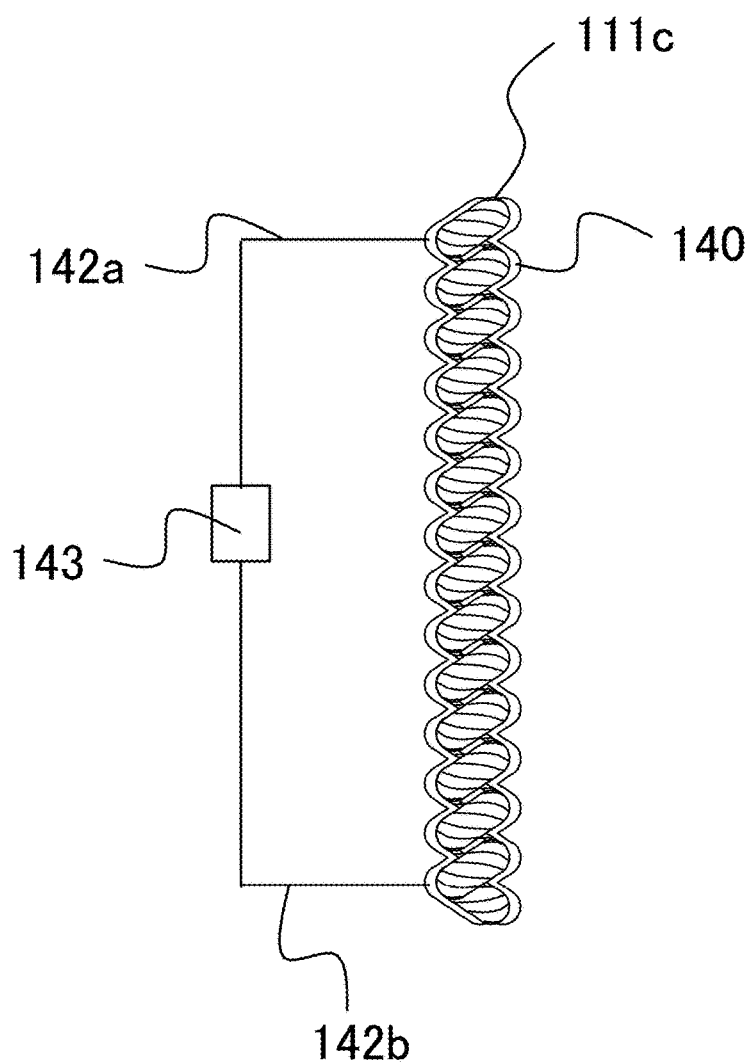
FIG. 2E shows a schematic view of the fiber 111c coated with a metal film 140.

As shown in FIG. 2E, the fiber 111c may be coated with a metal film 140. Electric wires 142a and 142b are electrically connected to the surfaces located at one end and the other end of the fiber 111c, respectively. Electric energy may be supplied through the electric wires 142a and 142b from a controller 143 which functions as the temperature regulator 130 to the metal film 140.

The temperature regulator 130 having the metal film 140 may be used in combination with the Peltier element. For example, the metal film 140 is heated by supply of electric energy, and thereby the fiber 111c is heated. The Peltier element having a shape of a thin plate cools the fiber 111c. The electric energy required for the Peltier element may be supplied from the controller 143.

(Actuator Operation)

Figures 3, 4:
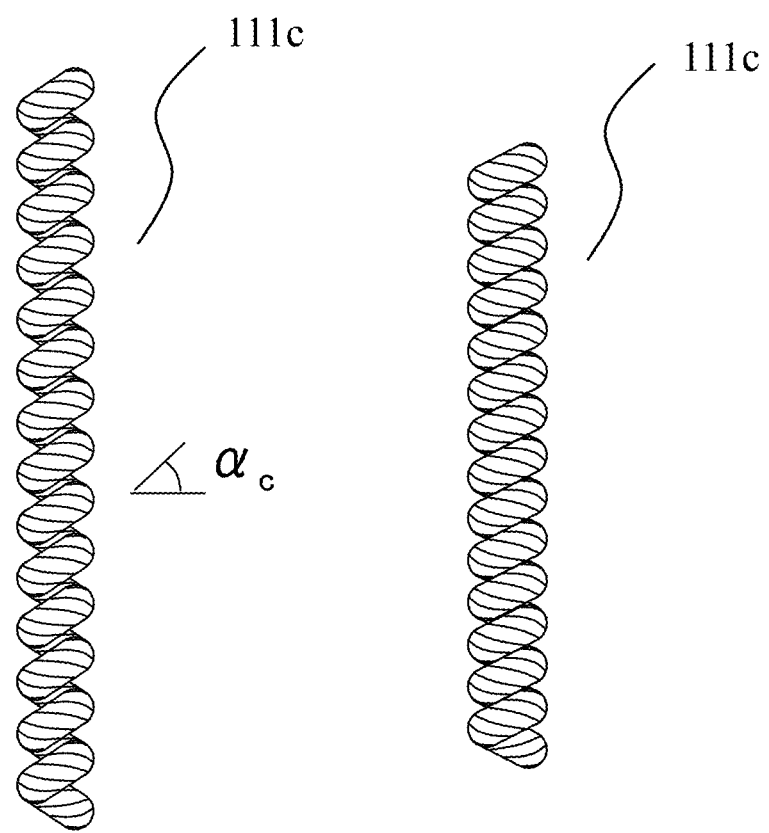
FIG. 3 shows a schematic view of a state of the fiber 111c before the fiber 111c is heated.
FIG. 4 shows a schematic view of a state of the fiber 111c after the fiber 111c is heated.

When the cylindrical coil formed of the folded fiber 111c is heated, the cylindrical coil is contracted along the coil axis 110LA. More specifically, when the fiber 111c is heated, the coil bias angle $\alpha_c$ is decreased. For this reason, the pitch p of the cylindrical coil is decreased. Compare FIG. 4 which shows the state of the fiber 111c after the fiber is heated to FIG. 3 which shows the state of the fiber 111c before the fiber 111c is heated. In this way, the folded fiber 111c having a shape of a cylindrical coil is contracted along the coil axis 110LA. When the fiber 111c is cooled, the fiber 111c is extended along the coil axis 110LA.

The cylindrical coil formed of the folded fiber 111c may be heated to a temperature of more than 30 degrees Celsius and not more than 100 degrees Celsius. In case of not more than 30 degrees Celsius, since the fiber 111c is heated insufficiently, the folded fiber 111c would not be contracted. In case of more than 100 degrees Celsius, the fiber 111c may be melted. It is desirable that the cylindrical coil is heated within a range of not less than 50 degrees Celsius and not more than 90 degrees Celsius.

The heated fiber 111c is cooled to a temperature of not more than 30 degrees Celsius. The fiber 111c may be cooled naturally under room temperature. Alternatively, the fiber 111c may be cooled by the cooler such as a Peltier element. The above-mentioned heating and cooling may be repeated.

As demonstrated in the examples which will be described later, the present inventors found that the fiber 111c formed of linear low-density polyethylene has a high displacement rate DR of not less than $0.38 \times 10^{-2}/°$ C., compared to a case where the folded fiber 111c is formed of another resin.

The displacement rate DR is defined by the following mathematical formula (I).

$$\text{(Displacement Rate DR)} = (x-y)/(x \cdot \Delta T) \quad \text{(I)}$$

where x represents a length of the fiber along the axis direction of the cylindrical coil before the fiber is heated, y represents a length of the fiber along the axis direction of the cylindrical coil after the fiber is heated, and $\Delta T$ represents a temperature difference of the folded fiber between before and after the fiber is heated.

As just described, when the folded fiber 111c is formed of linear low-density polyethylene, the displacement rate DR is a high value of $0.38 \times 10^{-2}/°$ C. On the other hand, in case where the folded fiber 111c is formed of a resin other than linear low-density polyethylene (e.g., high-density polyethylene or nylon 66), the displacement rate DR is a low value. For example, the fiber 111c formed of high-density polyethylene has a low displacement rate DR of $0.12 \times 10^{-2}/°$ C. The fiber 111c formed of nylon 66 has a low displacement rate DR of $0.096 \times 10^{-2}/°$ C.

EXAMPLES

Hereinafter, the present invention will be described in more detail with reference to the examples.

Inventive Example 1A

L-LDPE pellets (available from Sigma Aldrich Corporation) having a density of 0.918 g/cm³ were loaded into a melt extruder. While the temperature inside the melt extruder was maintained at 220 degrees Celsius, the L-LDPE was left at rest in the inside of the melt extruder for approximately 30 minutes. Then, the melted L-LDPE was pushed out of the nozzle attached to the tip of the melt extruder. The nozzle had a diameter of 1 millimeter. In this way, yarn formed of L-LDPE was obtained from the tip of the nozzle. The yarn was wound around a first roller (not shown) having a diameter of 5 centimeters. In this way, the yarn formed of L-LDPE (diameter: approximately 0.5 millimeters) was obtained. This yarn had an elastic coefficient of 0.16 GPa.

Next, one end of the yarn was bound to a second roller (not shown) having a diameter of 5 centimeters. A plate heated to 80 degrees Celsius was located between the first roller and the second roller. While the yarn was brought into contact with the surface of the plate, the yarn was supplied from the first roller and the yarn extended by the heat was wound around the second roller. In this way, the fiber 111a wound around the second roller was obtained. In other words, the extended yarn is the fiber 111a. The rotation speed of the first roller was 2 rpm. The rotation speed of the second roller was 20 rpm. In this way, the yarn was extended to obtain the fiber 111a. The fiber 111a had a diameter of 0.12 millimeters. FIG. 5A is a photograph showing the fiber 111a. In this way, the fiber 111a shown in FIG. 2A was obtained. The fiber 111a had an elastic coefficient of 2.5 GPa.

Figure 6A:
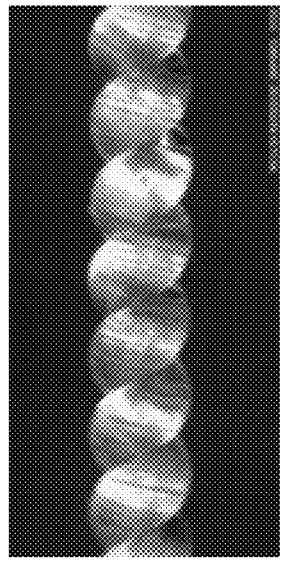
FIG. 6A is a photograph showing the folded fiber 111c obtained in the inventive example 1A.

Then, the fiber 111a was cut to obtain the fiber 111a having a length of 26 millimeters. While a tension was applied to the fiber 111, the fiber 111 was twisted to obtain the twisted fiber 111b shown in FIG. 2B. Furthermore, the fiber 111 was twisted to obtain the folded fiber 111c shown in FIG. 2C. In the inventive example 1A, the tension was 8 MPa. FIG. 6A is a photograph showing the folded fiber 111c obtained in the inventive example 1A. The length L3 of the folded fiber 111c was 9.7 millimeters.

The folded fiber 111c obtained in the inventive example 1A had a spring index C of 0.73.

Inventive Example 1B

In the inventive example 1B, an experiment similar to the inventive example 1A was conducted, except that the tension was 10 MPa. The folded fiber 111c obtained in the inventive example 1B had a spring index C of 0.52.

Inventive Example 1C

In the inventive example 1C, an experiment similar to the inventive example 1A was conducted, except that the tension was 17 MPa. The folded fiber 111c obtained in the inventive example 1C had a spring index C of 0.54.

Inventive Example 1D

In the inventive example 1D, an experiment similar to the inventive example 1A was conducted, except that the tension was 20 MPa. The folded fiber 111c obtained in the inventive example 1D had a spring index C of 0.50.

Inventive Example 1E

In the inventive example 1E, an experiment similar to the inventive example 1A was conducted, except that the tension was 30 MPa. The folded fiber 111c obtained in the inventive example 1E had a spring index C of 0.50.

Comparative Example 1A

In the comparative example 1A, an experiment similar to the inventive example 1A was conducted except the following matters (I)-(IV).

(I) In place of L-LDPE, used were pellets of low-density polyethylene (hereinafter, referred to as "LDPE", available from Sigma Aldrich Corporation) having a density of 0.906 g/cm$^3$.

(II) The temperature inside the melt extruder was maintained at 95 degrees Celsius.

(III) The temperature of the heated plate was 85 degrees Celsius.

(IV) The rotation speed of the second roller was 8 rpm.

FIG. 5B is a photograph showing the extended fiber 111a obtained in the comparative example 1A. This fiber 111a had a diameter of 0.1 millimeter and an elastic coefficient of 0.1 GPa.

While a tension of 5 MPa was applied to the fiber 111, the fiber 111a was twisted. However, before the fiber 111 was folded, namely, before the shape of the cylindrical coil was formed, the fiber 111a was broken. In other words, the fiber 111a was broken into two parts.

Comparative Example 1B

In the comparative example 1B, an experiment similar to the comparative example 1A was conducted, except that the tension was 10 MPa. Similarly to the case of the comparative example 1A, the fiber 111a was broken before the shape of the cylindrical coil was formed.

Comparative Example 1C

In the comparative example 1C, an experiment similar to the comparative example 1A was conducted, except that the rotation speed of the second roller was 12 rpm. However, the yarn was cleaved into two parts between the first roller and the second roller. Therefore, the fiber 111a was not obtained.

Comparative Example 2A

In the comparative example 2A, an experiment similar to the inventive example 1A was conducted except the following matters (I)-(III).

(I) In place of L-LDPE, used were pellets of high-density polyethylene (hereinafter, referred to as "HDPE", available from Sigma Aldrich Corporation) having a density of 0.96 g/cm$^3$.

(II) The temperature of the heated plate was 100 degrees Celsius.

(III) The rotation speed of the first roller and the second roller was 1 rpm and 25 rpm, respectively.

FIG. 5C is a photograph showing the extended fiber 111a obtained in the comparative example 2A. This fiber 111a had a diameter of 0.14 millimeters and an elastic coefficient of 1.5 GPa.

Figure 6B:
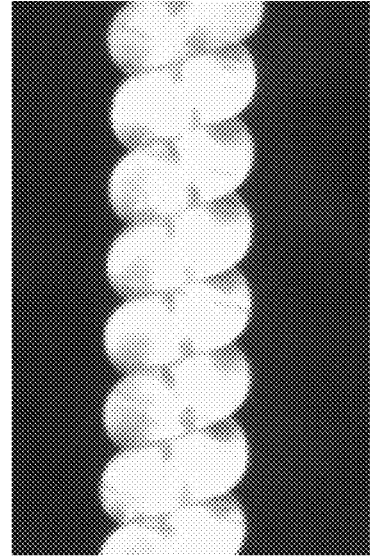
FIG. 6B is a photograph showing the folded fiber 111c obtained in the comparative example 2A.

Then, the fiber 111a was cut to obtain the fiber 111a having a length of 70 millimeters. While a tension of 10 MPa was applied to the fiber 111, the fiber 111 was twisted to obtain the twisted fiber 111b shown in FIG. 2B. Furthermore, the fiber 111 was twisted to obtain the folded fiber 111c shown in FIG. 2C. FIG. 6B is a photograph showing the folded fiber 111c obtained in the comparative example 2A. The length L3 of the folded fiber 111c was 13.3 millimeters.

The folded fiber 111c obtained in the comparative example 2A had a spring index C of 1.21.

Comparative Example 2B

In the comparative example 2B, an experiment similar to the comparative example 2A was conducted, except that the tension was 20 MPa. The folded fiber 111c obtained in the comparative example 2B had a spring index C of 1.03.

Comparative Example 2C

In the comparative example 2C, an experiment similar to the comparative example 2A was conducted, except that the tension was 30 MPa. In the comparative example 2C, the fiber 111a was obtained; however, the fiber 111 was broken during the twist before the shape of the coil was formed.

Comparative Example 3A

In the comparative example 3A, an experiment similar to the inventive example 1A was conducted except the following matters (I)-(IV).

(I) In place of L-LDPE, used were pellets of nylon 66 (available from Sigma Aldrich Corporation) having a density of 1.14 g/cm$^3$. After the pellets were left at rest in a vacuum oven maintained at 210 degrees Celsius for six hours, the pellets were loaded into the melt extruder.

(II) The temperature inside the melt extruder was maintained at 265 degrees Celsius.

(III) The temperature of the heated plate was 175 degrees Celsius.

(IV) The rotation speed of the first roller and the second roller was 5 rpm and 25 rpm, respectively.

FIG. 5D is a photograph showing the extended fiber 111a obtained in the comparative example 3A. This fiber 111a had a diameter of 0.12 millimeters and an elastic coefficient of 3.7 GPa.

Figure 6C:
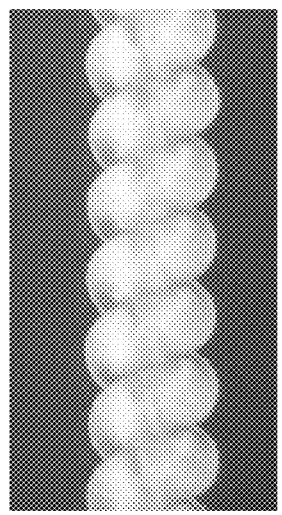
FIG. 6C is a photograph showing the folded fiber 111c obtained in the comparative example 3A.

Then, the fiber 111a was cut to obtain the fiber 111a having a length of 56 millimeters. While a tension of 17 MPa was applied to the fiber 111, the fiber 111 was twisted to obtain the twisted fiber 111b shown in FIG. 2B. Furthermore, the fiber 111 was twisted to obtain the folded fiber 111c shown in FIG. 2C. FIG. 6C is a photograph showing the folded fiber 111c obtained in the comparative example 3A. The length L3 of the folded fiber 111c was 12.1 millimeters.

The folded fiber 111c obtained in the comparative example 3A had a spring index C of 1.15.

Comparative Example 3B

In the comparative example 3B, an experiment similar to the comparative example 3A was conducted, except that the tension was 30 MPa. The folded fiber 111c obtained in the comparative example 3B had a spring index C of 1.1.

Comparative Example 3C

In the comparative example 3C, an experiment similar to the comparative example 3A was conducted, except that the tension was 45 MPa. In the comparative example 3C, the fiber 111 was obtained; however the fiber 111 was broken during the twist before the shape of the coil was formed.

(Thermomechanical Analysis)

Figure 7:
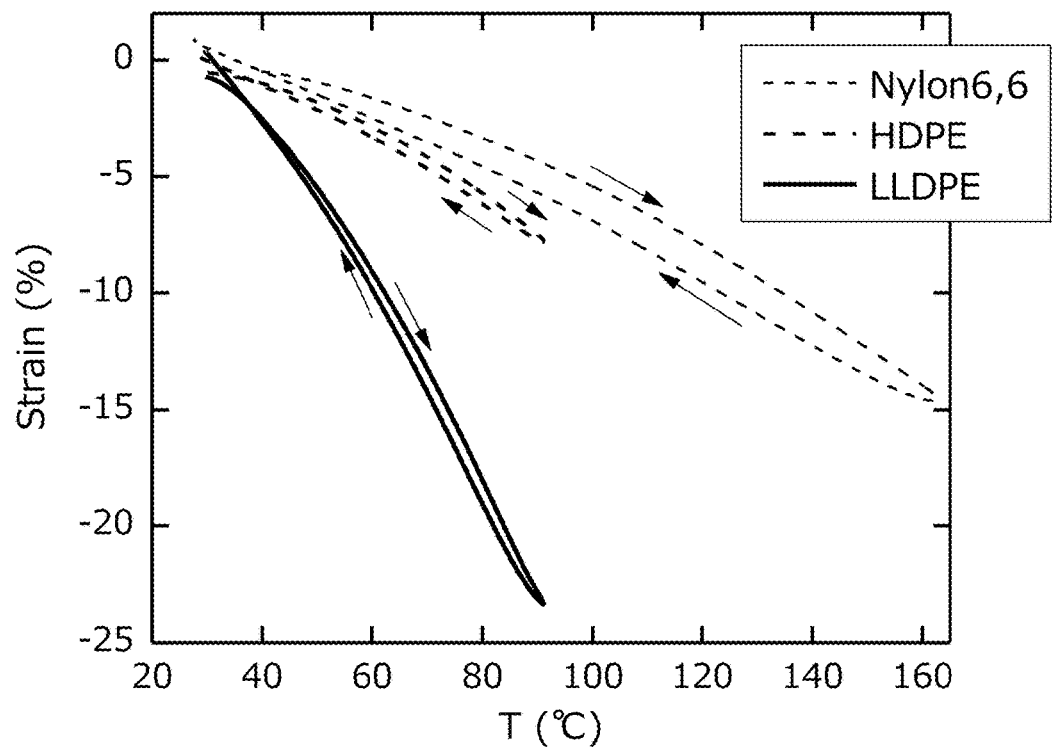
FIG. 7 is a graph showing thermomechanical properties of the fibers 111c obtained in the inventive example 1A, the comparative example 2A and the comparative example 3A.

The folded fibers 111c obtained in the inventive example 1A, the comparative example 2A, and the comparative example 3A were subjected to thermomechanical analysis. More specifically, the folded fibers 111c were loaded into a thermomechanical analysis device (available from Rigaku Corporation, trade name: TMA8310) to analyze the thermomechanical properties thereof. FIG. 7 is a graph showing the thermomechanical properties of the folded fibers 111c obtained in the inventive example 1A, the comparative example 2A, and the comparative example 3A.

In FIG. 7, the horizontal axis indicates temperature (Celsius). The vertical axis indicates strain. The strain is calculated in accordance with the following mathematical formula (II).

$$(\text{Strain}) = (x-y)/(x) \quad (II)$$

where x represents a length of the folded fiber along the axis direction of the cylindrical coil before the folded fiber is heated (namely, at a temperature of approximately 30 degrees Celsius), and y represents a length of the folded fiber along the axis direction of the cylindrical coil after the folded fiber is heated.

In other words, the following mathematical formula (III) is satisfied.

$$(\text{Displacement Rate DR}) = (\text{Strain})/\Delta T$$

where $\Delta T$ represents a temperature difference of the folded fiber between before and after the fiber is heated.

In the inventive example 1A, the length L3 of the folded fiber 111c was 9.7 millimeters. When the fiber 111c was heated to 90 degrees Celsius, the fiber 111c had a length L3 of 7.5 millimeters. In other words, when the fiber 111c was heated to 90 degrees Celsius, the fiber 111c was contracted in such a manner that the fiber 111c had a length L3 of 7.5 millimeters. Then, when the fiber 111c was cooled to 30 degrees Celsius, the length L3 of the fiber 111c returned to 9.7 millimeters.

In the inventive example 1A, the displacement rate DR was calculated as below.

$$\text{Displacement rate DR} = (9.7\text{ mm} - 7.5\text{ mm})/(9.7\text{ mm} \cdot (90° \text{C.} - 30° \text{C.})) = 0.38 \times 10^{-2}/° \text{C.}$$

In the comparative example 2A, the length L3 of the folded fiber 111c was 13.3 millimeters. Then, the folded fiber 111c was heated to 90 degrees Celsius. In the comparative example 2A, when the fiber 111c was heated to 90 degrees Celsius, the fiber 111c had a length L3 of 12.3 millimeters. When the fiber 111c was cooled to 30 degrees Celsius, the length L3 of the fiber 111c returned to 13.3 millimeters.

In the comparative example 2A, the displacement rate DR was calculated as below.

$$\text{Displacement rate DR} = (13.3\text{ mm} - 12.3\text{ mm})/(13.3\text{ mm} \cdot (90° \text{C.} - 30° \text{C.})) = 0.13 \times 10^{-2}/° \text{C.}$$

In the comparative example 3A, the folded fiber 111c had a spring index C of 1.15. The length L3 of the folded fiber 111c was 12.1 millimeters. Then, the folded fiber 111c was heated to 90 degrees Celsius. In the comparative example 3A, when the fiber 111c was heated to 90 degrees Celsius, the fiber 111c had a length L3 of 11.4 millimeters. When the fiber 111c was cooled to 30 degrees Celsius, the length L3 of the fiber 111c returned to 12.1 millimeters.

In the comparative example 3A, the displacement rate DR was calculated as below.

$$\text{Displacement rate DR} = (12.1\text{ mm} - 11.4\text{ mm})/(12.1\text{ mm} \cdot (90° \text{C.} - 30° \text{C.})) = 0.096 \times 10^{-2}/° \text{C.}$$

The following Table 1 and Table 2 show the results of the inventive examples and the comparative examples.

TABLE 1

|  | Materials of Fiber 111 | Tension (MPa) | Spring Index C |
|---|---|---|---|
| Inventive example 1A | L-LDPE | 8 | 0.73 |
| Inventive example 1B | L-LDPE | 10 | 0.52 |
| Inventive example 1C | L-LDPE | 17 | 0.54 |
| Inventive example 1D | L-LDPE | 20 | 0.50 |
| Inventive example 1E | L-LDPE | 30 | 0.50 |
| Comparative example 1A | LDPE | 5 | (broken) |
| Comparative example 1B | LDPE | 10 | (broken) |
| Comparative example 1C | LDPE | (Fiber was not obtained) | |
| Comparative example 2A | HDPE | 10 | 1.21 |
| Comparative example 2B | HDPE | 20 | 1.03 |
| Comparative example 2C | HDPE | 30 | (broken) |
| Comparative example 3A | Nylon 66 | 17 | 1.15 |
| Comparative example 3B | Nylon 66 | 30 | 1.1 |
| Comparative example 3C | Nylon 66 | 45 | (broken) |

TABLE 2

| | Materials of Fiber 111 | Length L3 (mm) at 30 degrees Celsius | Length L3 (mm) at 90 degrees Celsius | Displacement Rate (° C.$^{-1}$) |
|---|---|---|---|---|
| Inventive example 1A | L-LDPE | 9.7 | 7.5 | 0.38 × 10$^{-2}$ |
| Comparative example 2A | HDPE | 13.3 | 12.3 | 0.13 × 10$^{-2}$ |
| Comparative example 3A | Nylon 66 | 12.1 | 11.4 | 0.096 × 10$^{-2}$ |

As is clear from Table 1, the fiber formed of linear low-density polyethylene is not broken even when the spring index C is less than 1. However, it is impossible to form a cylindrical coil having a spring index C of less than 1 by twisting the fiber formed of low-density polyethylene, high-density polyethylene, or nylon 66.

As is clear from Table 2, the fiber 111c formed of linear low-density polyethylene had a high displacement rate DR of 0.38×10$^{-2}$/° C. On the other hand, the fibers 111c formed of high-density polyethylene or nylon 66 had low displacement rates DR of 0.12×10$^{-2}$/° C. and 0.096×10$^{-2}$/° C., respectively.

INDUSTRIAL APPLICABILITY

The actuator according to the present invention can be used as an artificial muscle.

REFERENTIAL SIGNS LIST

110LA Coil axis
111 Fiber
   111a Fiber which is neither twisted nor folded
   111b Fiber which is twisted, however, not folded.
   111c Fiber which is twisted and folded
   111LA Fiber axis
R1 Rotation direction of cylindrical coil
p Pitch of coil
d Diameter of fiber
D Mean diameter of cylindrical coil
D' External diameter of coil
L1 Length of fiber 111a
L2 Length of fiber 111b
L3 Length of fiber 111c
140 Metal film
142a Electric wire
142b Electric wire
143 Controller
$\alpha_c$ Coil bias angle
$\alpha_f$ Fiber bias angle
120 Base
121a First protrusion
121b Second protrusion
121c Through hole
122 Holding fixture
123 Rod
124 Hook
125 Slider

The invention claimed is:
1. An actuator, comprising:
a fiber; and
a temperature regulator capable of at least one of heating and cooling the fiber, wherein:
the fiber is twisted around a longitudinal axis thereof,
the fiber is folded so as to have a shape of a cylindrical coil,
the fiber is formed of linear low-density polyethylene,
the following mathematical formula (I) is satisfied:

$$D/d < 1 \quad (I)$$

where
D represents a mean diameter of the cylindrical coil; and
d represents a diameter of the fiber,
the fiber has a density of not less than 0.915 g/cm$^3$ and not more than 0.925 g/cm$^3$,
the fiber has a weight-average molecular weight of not less than 50 kg/mol and not more than 200 kg/mol,
the fiber is composed of ethylene monomer units each represented by the chemical structural formula —(CH$_2$—CH$_2$)$_n$—, where n is a natural number, and α-olefin monomer units each represented by the chemical structural formula —(CH$_2$—CHR)$_m$—, where m is a natural number, and R represents a hydrocarbon group,
each of the α-olefin monomer units has a carbon number of not less than 4 and not more than 8, and
a molar ratio of the α-olefin monomer units to the ethylene monomer units is not less than 2.5% and not more than 3.5%.
2. The actuator according to claim 1, wherein
the longitudinal axis of the fiber accords with a rotation direction of the cylindrical coil.
3. The actuator according to claim 1, wherein
one end of the fiber is a fixed end; and
the other end of the fiber is extendable along an axis direction of the cylindrical coil.
4. The actuator according to claim 1, further comprising:
a base; wherein
the base comprises a protrusion;
one end of the fiber is fixed to the protrusion; and
the other end of the fiber is extendable along an axis direction of the cylindrical coil.
5. The actuator according to claim 4, wherein
the other end of the fiber is provided with at least one of a plate-like slider, a pulley, and a guide tube; and
the least one of the plate-like slider, the pulley, and the guide tube is slidable on the base along the axis direction of the cylindrical coil.
6. The actuator according to claim 1, further comprising:
a base; wherein
the temperature regulator is located between the base and the fiber; and
the temperature regulator has a shape of a plate.
7. The actuator according to claim 1, wherein
the temperature regulator comprises a controller and a metal film;
the fiber is coated with the metal film; and
the controller supplies electric energy to the metal film.
8. The actuator according to claim 7, further comprising:
a base; wherein
the temperature regulator further comprises a Peltier element;
the Peltier element is located between the base and the fiber; and
the Peltier element has a shape of a plate.
9. The actuator according to claim 1, wherein the following mathematical formula (I) is satisfied:

$$(\text{Displacement Rate DR}) \geq 0.38 \times 10^{-2}/° C \quad (I)$$

where
(Displacement Rate DR) is equal to $(x-y)/(x \cdot \Delta T)$ where
x represents a length of the fiber along an axis direction of the cylindrical coil before the fiber is heated;
y represents a length of the fiber along the axis direction of the cylindrical coil after the fiber is heated; and
$\Delta T$ represents a temperature difference of the fiber between before and after the fiber is heated.

10. A method for extending and contracting a fiber; the method comprising:
(a) heating the fiber to contract the fiber, wherein
the fiber is twisted around a longitudinal axis thereof,
the fiber is folded so as to have a shape of a cylindrical coil,
the fiber is formed of linear low-density polyethylene,
the following mathematical formula (I) is satisfied:

$$D/d < 1 \tag{I}$$

where
D represents a mean diameter of the cylindrical coil; and
d represents a diameter of the fiber,
the fiber has a density of not less than 0.915 g/cm$^3$ and not more than 0.925 g/cm$^3$,
the fiber has a weight-average molecular weight of not less than 50 kg/mol and not more than 200 kg/mol,
the fiber is composed of ethylene monomer units each represented by the chemical structural formula $-(CH_2-CH_2)_n-$, where n is a natural number, and α-olefin monomer units each represented by the chemical structural formula $-(CH_2-CHR)_m-$, where m is a natural number, and R represents a hydrocarbon group,
each of the α-olefin monomer units has a carbon number of not less than 4 and not more than 8,
a molar ratio of the α-olefin monomer units to the ethylene monomer units is not less than 2.5% and not more than 3.5%, and
the fiber is contracted along an axis direction of the cylindrical coil; and
(b) cooling the fiber to extend the fiber,
wherein the fiber is extended along the axis direction of the cylindrical coil.

11. The method according to claim 10, wherein
in the step (a), the fiber is heated to a temperature of more than 30 degrees Celsius and not more than 100 degrees Celsius.

12. The method according to claim 10, wherein
in the step (b), the fiber is cooled to a temperature of not more than 30 degrees Celsius.

13. The method according to claim 10, wherein
the step (a) and the step (b) are repeated.

14. The method according to claim 10, wherein
in the step (a), the following mathematical formula (I) is satisfied:

$$\text{(Displacement Rate DR)} \geq 0.38 \times 10^{-2}/^\circ C. \tag{I}$$

where (Displacement Rate DR) is equal to $(x-y)/(x \cdot \Delta T)$ where
x represents a length of the fiber along the axis direction of the cylindrical coil before the fiber is heated;
y represents a length of the fiber along the axis direction of the cylindrical coil after the fiber is heated; and
$\Delta T$ represents a temperature difference of the fiber between before and after the fiber is heated.

* * * * *